US006919339B2

(12) United States Patent
Campbell et al.

(10) Patent No.: US 6,919,339 B2
(45) Date of Patent: Jul. 19, 2005

(54) ABCA-1 ELEVATING COMPOUNDS

(75) Inventors: Michael Campbell, Durham, NC (US); Prabha N. Ibrahim, Mountain View, CA (US); Jeff A. Zablocki, Mountain View, CA (US); Richard Lawn, San Francisco, CA (US)

(73) Assignee: CV Theapeutics, Inc., Palo Alto, CA (US)

(*) Notice: Subject to any disclaimer, the term of this patent is extended or adjusted under 35 U.S.C. 154(b) by 0 days.

(21) Appl. No.: 10/005,064

(22) Filed: Dec. 4, 2001

(65) Prior Publication Data

US 2002/0128266 A1 Sep. 12, 2002

Related U.S. Application Data

(60) Provisional application No. 60/313,274, filed on Aug. 17, 2001, and provisional application No. 60/251,916, filed on Dec. 7, 2000.

(51) Int. Cl.$^7$ ...................... C07D 251/16; A61K 31/53
(52) U.S. Cl. ...................... 514/245; 544/213
(58) Field of Search ........................ 544/213; 514/245

(56) References Cited

U.S. PATENT DOCUMENTS

| 2,937,172 | A | * | 5/1960 | Shapiro et al. ........... 260/249.9 |
| 3,845,770 | A | | 11/1974 | Theeuwes |
| 4,326,525 | A | | 4/1982 | Swanson et al. |
| 4,559,345 | A | | 12/1985 | Gomarasca et al. |
| 4,892,946 | A | * | 1/1990 | Levitt .......................... 544/321 |
| 4,902,514 | A | | 2/1990 | Barclay et al. |
| 4,992,445 | A | | 2/1991 | Lawter et al. |
| 5,001,139 | A | | 3/1991 | Lawter et al. |
| 5,023,252 | A | | 6/1991 | Hseih |
| 5,616,345 | A | | 4/1997 | Geoghegan et al. |
| 5,691,364 | A | | 11/1997 | Buckman et al. |
| 6,150,362 | A | | 11/2000 | Henkin et al. |

FOREIGN PATENT DOCUMENTS

| DE | 12 20 860 | | 7/1966 |
| DE | 195 36 891 | | 4/1997 |
| GB | 1384684 | * | 2/1975 |
| WO | WO 81/0320 | | 10/1981 |
| WO | WO 00/43369 | | 7/2000 |
| WO | WO 01/47897 | | 7/2001 |

OTHER PUBLICATIONS

Kozakiewicz, Chem. Abstract 130:267406, 1999.*
Pomarnacka et al., Chem. Abstract 130:153642, 1998.*
Kelarev et al., Chem. Abstract 130:68841, 1998.*
Silin et al., Chem. Abstract 129:260428, 1998.*
Dollinger et al., Chem. Abstract 270618, 1998.*
Hataba, CAPLUS Abstract No. 128:3618, 1997.*
Radics et al., CAPLUS Abstract 107:198262, 1987.*
Maekawa et al., CAPLUS Abstract 85:154963, 1976.*
Watanabe et al., CAPLUS Abstract 132:12332, 1999.*
Riebel et al., CAPLUS Abstract 128:282850, 1998.*
Lorenz et al., CAPLUS Abstract 127:262706, 1997.*
Takematsu et al., CAPLUS Abstract 112:179031, 1990.*
Abou–Ouf et al., CAPLUS Abstract 106:4981, 1987.*
Shapiro et al., CAOLD Abstract 54:19728f, 1960.*
Overberger et al., CAOLD Abstract 49:3980e, 1959.*

Walker, et al., "The Adenosine 5',5''', $P_1$, $P_4$–Tetraphosphate Receptor Is at the Cell Surface of Heart Cells," *Biochemistry*, 32, 14009–14014 (1993).

Smith, et al., Cyclic AMP Induces Apolipoprotein E Binding Activity and Promotes Cholesterol Efflux from a Macrophage Cell Line to Apolipoprotein Acceptors, *The Journal of Biological Chemistry*, vol. 271, pp. 30647–30655 (1996).

Francis, et al., "Defective Removal of Cellular Cholesterol and Phospholipids by Apolipoprotein A–1 in Tangier Disease,", *J. Clin. Invest.*, vol. 96, pp. 79–87 (1995).

Oram, et al., "Reduction in Apolipoprotein–mediated Removel of Cellular Lipids by Immortalization of Humans Fibroblasts and its Reversion by cAMP: Lack of Effect with Tangier Disease Cells," *Journal of Lipid Research*, vol. 40, pp. 1769–1781 (1999).

Cheung, et al., "Antioxidant Supplements Block the Response of HDL to Simvastatin–Niacin Therapy in Patients With Coronary Artery Disease and Low HDL," *Arterioscler Thromb. Vasc. Biol.*, 21(8) pp. 1320–26 (2001).

Kirtharides, et al., "Cholesterol Metabolism and Efflux in Human THP–1 Macrophages," *Thrombo Vasc. Biol.*, 18, pp. 1589–1599 (1998).

Falch, et al., "Substituted Heteroaromatic Anthranilic Acids with Antiinflammatory Activity," *Journal of Medicinal Chemistry*, vol. 11, pp. 608–611 (1968).

Ward, et al.., "Irreversible Enzyme Inhibitors 200.1 Active–Site–Directed Inhibitors of Deoxycytidine Kinase", *Journal of Medicinal Chemistry*, vol. 20, pp. 88–92 (1977).

Schwartz, et al., "ABC1 Gene Expression and ApoA–1–Medited Cholesterol Efflux are Regulated by LXR", *Biochemical and Biophysical Research Communications*, 274, pp. 794–802 (2000).

Chemical Abstracts, vol. 72, no. 13, Abstract No. 67000e, Kuroiki, et al. "Triazine Compounds", p. 410 (1970).

Chemical Abstracts, vol. 72, no. 13, Abstract No. 66998z, Mueller, et al. "Furylaminotriazines which promote growth of plants", p. 410 (1970).

(Continued)

*Primary Examiner*—Deepak Rao
(74) *Attorney, Agent, or Firm*—CV Therapeutics, Inc.

(57) ABSTRACT

The present invention provides compounds that elevate cellular expression of the ABCA-1 gene, promoting cholesterol efflux from cells and increasing HDL levels in the plasma of a mammal, in particular humans. The compounds are useful for treating coronary artery disease.

20 Claims, No Drawings

OTHER PUBLICATIONS

Taylor, et al., "The Rearrangement of 5–Nitroso–6–aminopyrimidines to s–Triazines", *J.Am. Chem. Soc.*, vol. 84, pp. 3744–3748 (1962).

Kuwano, et al., "Synthese von 1,3,5–Triazinen aus Aminosaure–Drivaten", *Argic. Biol.Chem.*, vol. 35, pp. 1572–1577 (1971).

Gohari, et al., "Studies on s–Triazinyl Aryl/Alkyl Sulphones", *J. Indian Chem. Soc.*, vol. 53, pp. 207–208 (1976).

Masquelin, et al. "Solution and Solid Phase Synthesis of Combinatorial Libraries of Trisubstituted 1,3,5–Triazines", *Heterocycles*, vol. 48, pp. 2489–2506 (1998).

Omokawa, et al., "Phyotoxic Activity of Substituted $_\alpha$–Methylbenzylamino Derivatives of 2–Chloro (or Methylthio)–4–ethylamino–s–triazines", *Agric. Biol. Chem.*, vol. 52, pp. 1047–1048 (1988).

Baker, et al., "Puromycin.Synthetic Studies. VI. Analogs of 6–Dimethylaminopurine", *J. Org. Chem.*, vol. 26, pp. 1793–1801 (1954).

Koppel, et al., "Pyrimidines I. Synthesis of Pyrimidinethiols", *J. Org. Chem.*, vol. 26, pp. 792–803 (1961).

Asthana, et al., "Synthesis of 9–aryl/pyrimidyl/alkyl–subsituted–(oxy/amino/carbonyl)–acridines and 1,3–bis(9–acridinyl)propan–2–ols as potential anticancer agents", *Indian Journal of Chemistry*, vol. 30B, pp. 853–858 (1991).

Okafor, et al., "Studies in the Heterocyclic Series. XVI. Open Azaphenothiazines as New Central Nervous System Depressants", *Chem. Pharm. Bull*, vol. 30, pp. 302–318 (1982).

Kelarev, et al., "Synthesis and Properties of sym–Triazine Derivatives", *Chem. Hetercycl. Compd.*, vol. 23, pp. 1118–1123, (1987).

Podzigun et al., "Chemical Properties of Acylated Derivatives of 4,6–Diamino–2–Mercaptopyrimidine", *Bull. Acad. Sci. USSR Div. Chem. Sci.*, vol. 29, pp. 1820–1823.

Database Crossfire Beilstein, Online Beilstein Institut zur Foerderung der Wissenschaftern, Frankfurt, am Main, DE: XP002203489, Database–Accession no. 649727, 1962.

Database Crossfire Beilstein, Online Beilstein Institut zur Foerderung der Wissenschaftern, Frankfurt, am Main, DE: XP002203490, Database–Accession nos. 825556, 835148, 1988.

Database Crossfire Beilstein, Online Beilstein Institut zur Foerderung der Wissenschaftern, Frankfurt, am Main, DE: XP002203491, Database–Accession no. 4554677, 1997.

Database Crossfire Beilstein, Online Beilstein Institut zur Foerderung der Wissenschaftern, Frankfurt, am Main, DE: XP002203492, Database–Accessions nos. 847903, 858797, 1988.

Database Crossfire Beilstein, Online Beilstein Institut zur Foerderung der Wissenschaftern, Frankfurt, am Main DE: XP002203493, Database–Accession no. 590307, 1988.

Database Crossfire Beilstein, Online Beilstein Institut zur Foerderung der Wissenschaftern, Frankfurt, am Main, DE: XP002203494, Database–Accession nos. 610033, 8260251, 8261917, 8263806, 8264837, 8265543, 8265549, 8265662, 8265677, 8268675, 8274019, 8290516, 1988.

Database Crossfire Beilstein, Online Beilstein Institut zur Foerderung der Wissenschaftern, Frankfurt, am Main, DE: XP002203495, Database–Accession nos. 6869560, 6870711, 6871427, 6872174, 6894394, 1994.

Database Crossfire Beilstein, Online Beilstein Institut zur Foerderung der Wissenschaftern, Frankfurt, am Main, DE: XP002203496, Database–Accession nos. 22301, 37158, 1988.

Database Crossfire Beilstein, Online Beilstein Institut zur Foerderung der Wissenschaftern, Frankfurt, am Main, DE: XP002203497, Database–Accession no. 721058, 1988.

Database Crossfire Beilstein, Online Beilstein Institut zur Foerderung der Wissenschaftern, Frankfurt, am Main, DE: XP002203498, Database–Accession no. 4879840, 1993.

Database Crossfire Beilstein, Online Beilstein Institut zur Foerderung der Wissenschaftern, Frankfurt, am Main, DE: XP002203499, Database–Accession nos. 5571913, 5579402, 1993.

Database Crossfire Beilstein, Online Beilstein Institut zur Foerderung der Wissenschaftern, Frankfurt, am Main, DE: XP002203500 Database–Accession nos. 6410850, 6425583, 6434370, 1994.

Database Chemcats Online, Chemical Abstract Service, Columbus, Ohio, XP002203501, Order Nos.: 0L–567S, 10L–566S, 10L–565S, 10L–561S, 10L–560S, 10L–549S, 10L–525S, 10L–523S, 10L–502S, 2001.

* cited by examiner

ABCA-1 ELEVATING COMPOUNDS

This application claims priority to U.S. Provisional Application Ser. Nos. 60/251916 filed on Dec. 7, 2000 and 60/313274 filed on Aug. 17, 2001.

FIELD OF THE INVENTION

The present invention relates to compounds useful for raising cellular ABCA-1 production in mammals, and to methods of using such compounds in the treatment of coronary artery diseases. The invention also relates to methods for the preparation of such compounds, and to pharmaceutical compositions containing them.

BACKGROUND OF THE INVENTION

Cholesterol is essential for the growth and viability of higher organisms. It is a lipid that modulates the fluidity of eukaryotic membranes, and is the precursor to steroid hormones such as progesterone, testosterone, and the like. Cholesterol can be obtained from the diet, or synthesized internally in the liver and the intestines. Cholesterol is transported in body fluids to specific targets by lipoproteins, which are classified according to increasing density. For example, low density lipoprotein cholesterol (LDL) is responsible for transport of cholesterol to and from the liver and to peripheral tissue cells, where LDL receptors bind LDL, and mediate its entry into the cell.

Although cholesterol is essential to many biological processes in mammals, elevated serum levels of LDL cholesterol are undesirable, in that they are known to contribute to the formation of atherosclerotic plaques in arteries throughout the body, which may lead, for example, to the development of coronary artery diseases. Conversely, elevated levels of high density lipoprotein cholesterol (HDL-C) have been found, based upon human clinical data, and animal model systems, to protect against development of coronary diseases.

In general, excess cholesterol is removed from the body by a pathway involving high density lipoproteins (HDLs). Cholesterol is "effluxed" from cells by one of two processes—either by passive transfer to mature HDL, or an active transfer to apolipoprotein A-1. The latter process is mediated by a protein known as ATP binding cassette transporter 1 (ABC-1, or alternatively referenced as ABCA-1). In the latter process, lipid-poor HDL precursors acquire phospholipid and cholesterol, which leads to increased plasma levels of mature HDL particles. HDL cholesterol is eventually transported to the liver in a process known as "reverse cholesterol transport", where it is either recycled or excreted as bile.

One method of treatment aimed at reducing the risk of formation of atherosclerotic plaques in arteries relates to decreasing plasma lipid levels. Such a method includes diet changes, and/or treatment with drugs such as derivatives of fibrinc acid (clofibrate, gemfibrozil, and fenofibrate), nicotinic acid, and HMG-CoA reductase inhibitors, such as mevinolin, mevastatin, pravastatin, simvastatin, fluvastatin, and lovastatin, which reduce plasma LDL cholesterol levels by either inhibiting the intracellular synthesis of cholesterol or inhibiting the uptake via LDL receptors. In addition, bile acid-binding resins, such as cholestyrine, colestipol and probucol decrease the level of LDL-cholesterol by reducing intestinal uptake and increasing the catabolism of LDL-cholesterol in the liver.

It is desired to provide alternative therapies aimed at reducing the risk of formation of atherosclerotic plaques in arteries, especially in individuals deficient in the removal of cholesterol from artery walls via the HDL pathway. Given that HDL levels are generally related to the expression of ABCA-1, one method of increasing HDL levels would be to increase the expression of ABCA-1. Accordingly, it is desired to provide compounds that are potent stimulators of the expression of ABCA-1 in mammals, thus increasing cholesterol efflux and raising HDL cholesterol levels in blood. This would be useful for the treatment of various disease states characterized by low HDL levels, in particular coronary artery disease.

It has also been shown that a combination of a drug that decreases LDL cholesterol levels and a drug that increases HDL cholesterol is beneficial; see, for example, Arterioscler., Thromn., Vasc. Biol. (2001), 21(8), 1320–1326, by Marian C. Cheung et al. Accordingly, it is also desired to provide a combination of a compound that stimulates the expression of ABCA-1 with a compound that lowers LDL cholesterol levels.

It should be noted it has also been shown that raising ABCA-1 production in macrophages locally reduces cholesterol deposition in coronary arteries without significantly raising plasma HDL cholesterol. In this instance, raising ABCA-1 expression is beneficial even in the absence of increased HDL cholesterol.

SUMMARY OF THE INVENTION

Accordingly, it is an object of this invention to provide compounds that elevate cellular expression of the ABCA-1 gene in a mammal. Accordingly, in a first aspect, the invention relates to compounds of Formula I useful for increasing ABCA-1 expression:

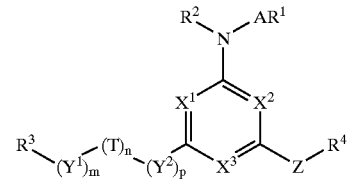

Formula I wherein:

m, n and p are independently 0 or 1;

A is —C($Z^1$)—, —C($Z^1$)-NH—, $SO_2$, or a covalent bond;
  where $Z^1$ is oxygen or sulfur;

$R^1$ is hydrogen, optionally substituted alkyl, optionally substituted alkenyl, optionally substituted alkynyl, optionally substituted cycloalkyl, optionally substituted heterocyclyl, optionally substituted aryl, or optionally substituted heteroaryl;

$R^2$ is hydrogen, alkyl, or cycloalkyl; or $R^1$, $R^2$ and A when taken together with the nitrogen atom to which they are attached form a nitrogen bearing heterocycle;

$R^3$ is optionally substituted alkyl, optionally substituted cycloalkyl, optionally substituted heterocyclyl, optionally substituted aryl, or optionally substituted heteroaryl;

$R^4$ is hydrogen, optionally substituted alkyl, optionally substituted cycloalkyl, optionally substituted heterocyclyl, optionally substituted aryl, or optionally substituted heteroaryl;

T is —O—, —S(O)$_q$, or —NR$^5$—;
  in which q is 0, 1, or 2, and $R^5$ is hydrogen, optionally substituted alkyl, optionally substituted cycloalkyl, optionally substituted heterocyclyl, optionally substituted aryl, or optionally substituted heteroaryl;

$X^1$, $X^2$, and $X^3$ are independently —$CR^6$ or nitrogen, in which $R^6$ is hydrogen, optionally substituted alkyl, optionally substituted cycloalkyl, optionally substituted heterocyclyl, optionally substituted aryl, or optionally substituted heteroaryl;

with the proviso that at least one of $X^1$, $X^2$, and $X^3$ is nitrogen.

$Y^1$ is lower alkylene or carbonyl;

$Y^2$ is lower alkylene or oxygen; and

Z is sulfur, oxygen, or —$NR^5$—, comprising administering to a mammal in need thereof a therapeutically effective dose of a compound of Formula I. Such diseases include, but are not limited to, diseases of the artery, in particular coronary artery disease.

In a second aspect, the invention relates to a method for using the compounds of Formula I in the treatment of a disease or condition in a mammal that can be usefully treated with a compound that elevates serum levels of HDL cholesterol, comprising administering to a mammal in need thereof a therapeutically effective dose of a compound of Formula I. Such diseases include, but are not limited to, diseases of the artery, in particular coronary artery disease.

In a third aspect, the invention relates to a method for using the compounds of Formula I in the treatment of a disease or condition in a mammal that can be usefully treated with a compound that promotes cholesterol efflux from cells, comprising administering to a mammal in need thereof a therapeutically effective dose of a compound of Formula I. Such diseases include, but are not limited to, diseases of the artery, in particular coronary artery disease.

In a fourth aspect, the invention relates to a method for using the compounds of Formula I in the treatment of a disease or condition characterized by low HDL-C in a mammal that can be usefully treated with a compound that elevates serum levels of HDL-C, comprising administering to a mammal in need thereof a therapeutically effective dose of a compound of Formula I. Such diseases include, but are not limited to, diseases of the artery, in particular coronary artery disease.

In a fifth aspect, the invention relates to a method for using the compounds of Formula I in the treatment of a condition related to coronary artery disease in a mammal that can be usefully treated with a combination of a compound that elevates serum levels of HDL cholesterol and a compound that lowers LDL cholesterol, comprising administering to a mammal in need thereof a therapeutically effective dose of a compound of Formula I and a compound that lowers LDL cholesterol.

A sixth aspect of this invention relates to pharmaceutical formulations, comprising a therapeutically effective amount of a compound of Formula I and at least one pharmaceutically acceptable excipient.

A seventh aspect of this invention relates to methods of preparing the compounds of Formula I.

Definitions and General Parameters

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-pentyl, 2-methylbutyl, n-hexyl, n-decyl, tetradecyl, and the like.

The term "substituted alkyl" refers to:

1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, aminothiocarbonylamio, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or 2) an alkyl group as defined above that is interrupted by 1–5 atoms or groups independently chosen from oxygen, sulfur and —$NR_a$—, where $R_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or 3) an alkyl group as defined above that has both from 1 to 5 substituents as defined above and is also interrupted by 1–5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1–5 atoms as defined for substituted alkyl, or a lower alkyl group as defined above that has both from 1 to 5 substituents as defined above and is also interrupted by 1–5 atoms as defined above.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—CH2-), ethylene (—CH2CH2-), the propylene isomers (e.g., —CH2CH2CH2- and —CH($CH_3$)CH2-) and the like.

The term "lower alkylene" refers to a diradical of a branched or unbranched saturated hydrocarbon chain, preferably having from 1 to 6 carbon atoms.

The term "substituted alkylene" refers to:

(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or (2) an alkylene group as defined above that is interrupted by 1–5 atoms or groups independently chosen from oxygen, sulfur and $NR_a$—, where $R_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both from 1 to 5 substituents as defined above and is also interrupted by 1–20 atoms as defined above. Examples of substituted alkylenes are chloromethylene (—CH(Cl)-), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—),1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH═CH$_2$), 1-propylene or allyl (—CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH₂.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF₃, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2. Such heteroaryl groups can have a single ring (e.g., pyridyl or furyl) or multiple condensed rings (e.g., indolizinyl, benzothiazolyl, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. All substituents may be optionally further substituted by alkyl, alkoxy, halogen, CF₃, amino, substituted amino, cyano, or —S(O)$_n$R, in which R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The definitions include the characterization that "R¹, R² and A when taken together with the nitrogen atom to which they are attached form a nitrogen bearing heterocycle". This definition refers to the possibility that R¹, R² and A when taken together with the nitrogen atom to which they are attached represent a 5, 6 or 7 membered cyclic amide, cyclic urea, cyclic thioamide, cyclic thiourea, or a cyclic sulfonamide, of the formula:

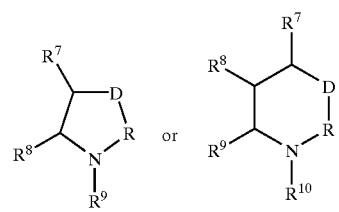

in which R is C(O), C(S), or SO₂, D is —C— or —NH—, and R⁷, R⁸, R⁹ and R¹⁰ are independently hydrogen or lower alkyl.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula. "Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R-S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "coronary artery disease" means a chronic disease in which there is a "hardening" (atherosclerois) of the coronary arteries.

The term "atherosclerosis" refers to a form of arteriosclerosis in which deposits of yellowish plaques containing cholesterol, lipoid material, and lipophages are formed within the intima and innner media of large and medium-sized arteries.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $X^1$, $X^2$, and $X^3$ are N, Z is sulfur, $R^1$ and $R^2$ are hydrogen, $R^3$ is 4-(tert-butyl)phenyl, $R^4$ is n-pentyl, A is a covalent bond, T is oxygen, in $(Y^1)_n$ n is 0, and $(Y^1)_n$ is methylene.

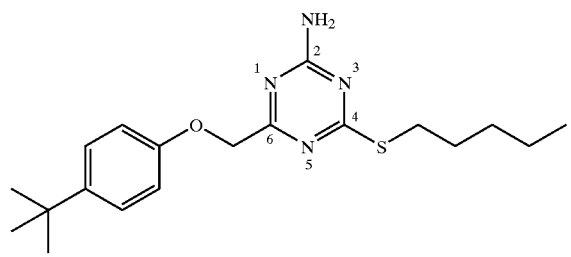

which is named: 6-{[4-(tert-butyl)phenoxy]methyl}-4-pentylthio-1,3,5-triazine-2-ylamine.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

An example of a method for preparing the compounds of Formula I is shown in Reaction Scheme I.

REACTION SCHEME I

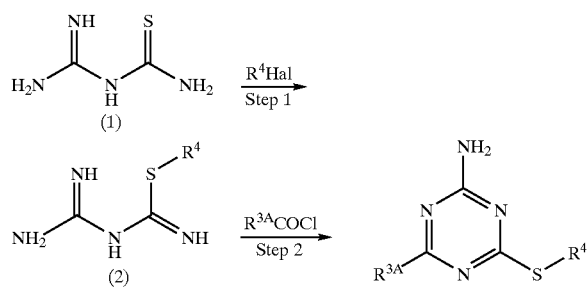

where $R^{3A}$ represents $R^3$—$Y^1$-T-$Y^2$—, and Hal is chloro, bromo, or iodo.

Step 1—Preparation of Formula (2)

The compound of formula (2) is prepared by reaction of the compound of formula (1) (2-imino-4-thiobiurea), a commercially available compound, with $R^4$Hal, in which $R^4$ is as defined above and Hal is chloro, bromo, or iodo. The reaction is carried out in an inert solvent, for example tetrahydrofuran, at room temperature, for about 10–48 hours. When the reaction is substantially complete, the next reaction is carried out with no purification.

Step 2—Preparation of Formula (3)

The compound of formula (3) is prepared by reaction of the compound of formula (2) with an acid chloride of the formula $R^{3A}C(O)Cl$ (in which $R^{3A}$ represents $R^3$—$Y^1$-T-$Y^2$—as defined above), in the presence of a base, preferably a tertiary organic base. The acid chloride is added in an inert solvent, preferably tetrahydrofuran, followed by the tertiary base, at about room temperature, and the mixture stirred for about 10–48 hours. When the reaction is substantially complete, the product of formula (3) is isolated by conventional means, for example by removal of solvent under reduced pressure and chromatographing the residue on silica gel.

Starting Materials

Many compounds of formula $R^{3A}C(O)Cl$, which is required in Step 2 above, are commercially available, or may be prepared by means well known in the art. For example, the preparation of a compound of formula $R^{3A}C(O)Cl$ in which $R^3$—$Y^1$-T-$Y^2$—is phenoxymethyl (i.e., $R^3$ is phenyl, $Y^1$ is a covalent bond, T is oxygen, and $Y^2$ is methylene) is shown in Reaction Scheme II.

REACTION SCHEME II

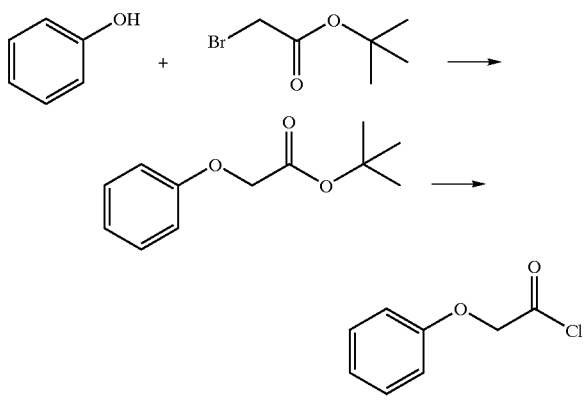

A similar reaction sequence can be used to prepare compounds of formula $R^{3A}C(O)Cl$, which is used to prepare a compound of Formula I in which T is sulfur.

Preparation of Compounds of Formula I in which T is Nitrogen.

A different reaction sequence is required to prepare compounds of Formula I in which T is nitrogen, as shown in Reaction Scheme III.

REACTION SCHEME III

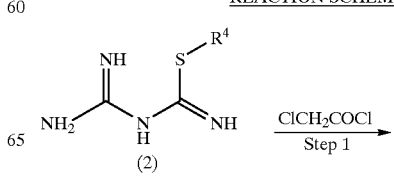

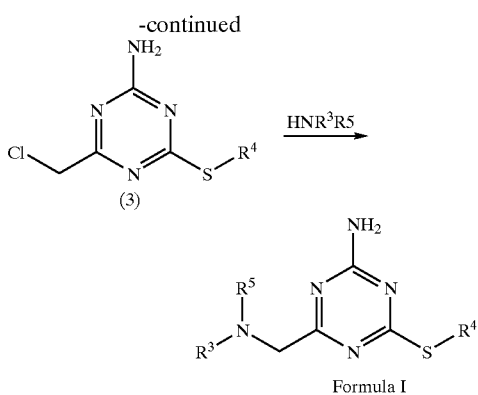

Step 1—Preparation of Formula (3)

The compound of formula (3) is prepared by reaction of the compound of formula (2) with chloroacetyl chloride, in the presence of a base, preferably a tertiary organic base. The acid chloride is added in an inert solvent, preferably tetrahydrofuran, followed by the tertiary base, at about room temperature, and the mixture stirred for about 10–48 hours. When the reaction is substantially complete, the product of formula (3) is isolated by conventional means, for example by removal of solvent under reduced pressure and chromatographing the residue on silica gel.

Step 2—Preparation of Formula I where T is NR

The compound of formula (3) is reacted with an amine of the formula $R^3R^5NH$ in the presence of a base, preferably a tertiary organic base, in an inert solvent, preferably tetrahydrofuran. The reaction is carried out at about 50–100° C., for about 10–48 hours, preferably about 16 hours. When the reaction is substantially complete, the product of Formula I is isolated by conventional means, for example by removal of solvent under reduced pressure and chromatographing the residue on silica gel.

Preparation of Compounds of Formula I in which T is Oxygen or Sulfur

Compounds of Formula I where Z is oxygen or sulfur may be prepared as shown in Reaction Scheme IIIA.

REACTION SCHEME IIIA

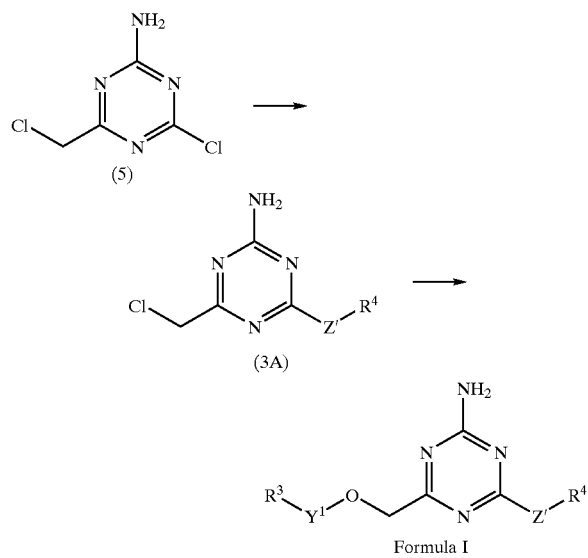

where Z' is oxygen of sulfur.

The starting material of formula (5) is well known in the art, and may be prepared as described in Yakugaki Zasshi (1975), 95(5), 521–30. Reaction of the compound of formula (5) with an anion of a compound of formula $R^4Z'H$, for example formed by reaction with sodium hydride, in an inert solvent, preferably displaces the ring chlorine to provide a compound of formula (3A). This intermediate can be further reacted as shown in Reaction Scheme III to give a compound of Formula I in which T is nitrogen. Alternatively, reaction of a compound of formula (3A) with an anion of a compound of formula $R^3$—$(Y^1)_n$ OH or $R^3$—$(Y^1)_n$ SH provides compound of Formula I in which T is oxygen or sulfur, $R^1$ and $R^2$ are both hydrogen, and A is a covalent bond. This compound of formula (3A) can be further converted to a compound of Formula I in which $R^1$ is not hydrogen, as shown in the Reaction Schemes above.

Preparation of Compounds of Formula I in which $X^1$ and $X^2$ are Nitrogen and $X^3$ is CH A reaction sequence for the preparation of compounds of Formula I in which $X^2$ and $X^3$ are nitrogen and $X^1$ is CH is shown in Reaction Scheme IV.

REACTION SCHEME IV

The compound of formula (4), which is commercially available, is reacted with a strong base, preferably sodium hydride, followed by an acid chloride of the formula $R^3C(O)$Halo in the presence of a base, preferably a tertiary organic base, in an inert solvent, preferably tetrahydrofuran. The reaction is carried out at about 50–100° C., for about 10–48 hours, preferably about 16 hours. When the reaction is substantially complete, the product of Formula I is isolated by conventional means, for example by removal of solvent under reduced pressure and chromato graphing the residue on silica gel.

Preparation of Compounds of Formula I in which A is —C($Z^1$)-.

A reaction sequence for the preparation of compounds of Formula I in which A is —C($Z^1$)-, where $Z^1$ is oxygen or hydrogen, is shown in Reaction Scheme V.

REACTION SCHEME V

-continued

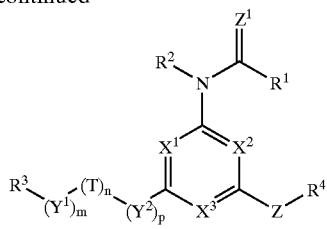

The compound of Formula I in which A is a covalent bond and R¹ is hydrogen is initially reacted with a strong base, preferably sodium hydride. The reaction is carried out in an inert solvent, preferably tetrahydrofuran, at a temperature of about 0° C., for about 1–30 minutes. A compound of formula R¹C(X¹)Cl, where X¹ is oxygen or sulfur, is then added, and the mixture allowed to warm to about room temperature for about 8–24 hours. When the reaction is substantially complete, the product of Formula I in which A is —C(X¹)— is isolated by conventional means, for example by removal of the solvent under reduced pressure, followed by chromatography of the residue on silica gel.

Preparation of Compounds of Formula I in which A is —C(Z¹)-NH—

A reaction sequence for the preparation of compounds of Formula I in which A is —C(Z¹)-NH—, where Z¹ is oxygen or sulfur, is shown in Reaction Scheme VI.

REACTION SCHEME VI

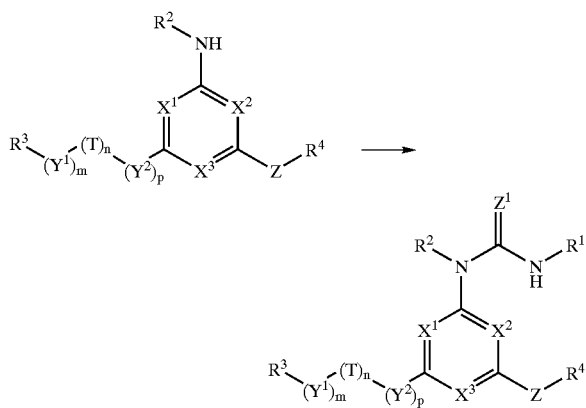

The compound of Formula I in which A is a covalent bond and R¹ is hydrogen is reacted with an isocyanate or isothiocyanate of formula R¹NCX¹, where X¹ is oxygen or sulfur, in the presence of a catalytic amount of 4-dimethylaminopyridine (DMAP), and a tertiary base, preferably triethylamine. The reaction is carried out in an inert solvent, for example acetonitrile, at a temperature of about 0–30° C., preferably about room temperature, for about 4–24 hours. When the reaction is substantially complete, the product of Formula I in which A is —C(X¹)—NH— is isolated by conventional means, for example by removal of the solvent under reduced pressure, followed by chromatography of the residue on silica gel.

Utility, Testing and Administration

General Utility

The compounds of Formula I stimulate the expression of ABCA-1 in mammalian cells, thus increasing cholesterol efflux and raising HDL levels in plasma. Therefore, the compounds of Formula I are useful for treating conditions related to high cholesterol/low HDL levels in mammals, including, but not limited to, coronary artery disease, including that produced by diabetes, and the like.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modem Pharmaceutics", Marcel Dekker, Inc. 3$^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

A. Preparation of a Compound of Formula (2) in which $R^4$ is Pentyl

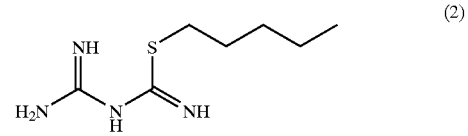

To a suspension of 2-imino-4-thiobiurea (3 g, 25.4 mmole) in dry tetrahydrofuran (100 ml) 1-bromopentane (4.6 g, 3.8 ml, 30.4 mmole) was added and stirred at room temperature for 16 hours, to provide a solution of amino (iminopentylthiomethyl)-carboxamidine, a compound of formula (2) in which $R^4$ is pentyl, in tetrahydrofuran. The solution was converted to a compound of Formula I with no further purification.

B. Preparation of a Compound of Formula (2), Varying $R^4$

Similarly, following the procedure of 1A above, but replacing bromopentane by other compounds of formula $R^4$Hal, other compounds of formula (2) were prepared in which $R^4$ is methyl, ethyl, n-propyl, isopropyl, n-butyl, sec-butyl, t-butyl, 3-methylpropyl, benzyl, and 4-t-butylbenzyl.

C. Preparation of a Compound of Formula (2), Varying $R^4$

Similarly, following the procedure of 1A above, but replacing bromopentane by other compounds of formula $R^4$Hal, the following compounds of formula (2) are prepared:

amino[imino(3-methoxypropyl)thiomethyl]-carboxamidine;
amino[imino(3-hydroxypropyl)thiomethyl]-carboxamidine;
amino(iminocyclopropylthiomethyl)-carboxamidine;
amino(iminocyclopentylthiomethyl)-carboxamidine;
amino(iminocyclopentylmethylthiomethyl)-carboxamidine;
amino(iminocyclohexylthiomethyl)-carboxamidine
amino[imino(thieny-2-yl)thiomethyl]-carboxamidine;
amino[imino(isoxazol-3-yl)thiomethyl]-carboxamidine;
amino[imino(furan-2-yl)thiomethyl]-carboxamidine;
amino[imino(pyrid-2-yl)thiomethyl]-carboxamidine;
amino{[2-(4-chlorophenyl)ethylthio)iminomethyl}-carboxamidine;
amino{[2-(4-tert-butylphenoxy)ethylthio)iminomethyl}-carboxamidine;
amino{[2-(4-trifluoromethylphenoxy)methylthio)iminomethyl}-carboxamidine;
amino{[2-(4-fluorophenoxy)ethylthio)iminomethyl}-carboxamidine; and
amino{[2-(3,5-dichlorophenoxy)methylthio)iminomethyl}-carboxamidine;

D. Preparation of a Compound of Formula (2), Varying $R^4$

Similarly, following the procedure of 1A above, but replacing bromopentane by other compounds of formula $R^4$Hal, any compound of formula (2) may be prepared.

EXAMPLE 2

Preparation of a Compound of Formula I

A. Preparation of a Compound of Formula I in which m is 0, n and p are 1, $R^1$ and $R^2$ are Hydrogen, $R^3$ is 4-t-butylphenyl, $R^4$ is Pentyl, T is Oxygen, A is a Covalent Bond, $X^1$, $X^2$, and $X^3$ are All Nitrogen, m is 0, n and p are Both 1, and Z is Sulfur

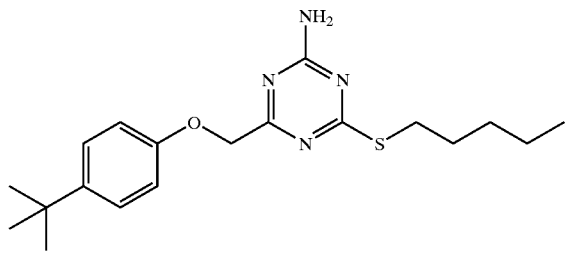

1) To a solution of oxalyl chloride in dichloromethane (25 ml, 2M) 4-t-butylphenoxyacetic acid (5.2 g, 25 mmole), prepared as shown in Reaction Scheme II, was added and cooled in an ice water bath. Anhydrous N,N-dimethylformamide (5 drops) was added to the solution, which was stirred at 0° C. for 30 minutes. The reaction mixture was allowed to warm up to room temperature and stirred until gas evolution stopped, concentrated under reduced pressure and the residue was twice azeotroped with toluene to give a solution of 2-(4-t-butylphenoxy) acetyl chloride. 2) To a solution of amino (iminopentylthiomethyl)-carboxamidine, a compound of formula (2), was added a solution of 2-(4-t-butylphenoxy) acetyl chloride in anhydrous tetrahydrofuran (25 ml) followed by anhydrous N,N-diisopropylethylamine (9.75 mL, 56 mmole) and the resulting mixture stirred at room temperature for 16 hours. The reaction mixture was concentrated under reduced pressure and the residue dissolved in ethyl acetate (150 mL) and washed with water (3×50 mL), 10% NaOH (2×25 mL), brine (1×50) and dried over anhydrous sodium sulfate. The solvent was removed under reduced pressure and the residue purified on silica gel using a hexane/ethyl acetate gradient (10% to 40% ethyl acetate) to give N-(6-{[4-(tert-butyl)phenoxy]methyl}-4-pentylthio-1,3,5-triazine-2-ylamine, a compound of Formula I, as a white solid. (M+1)=361.2.

B. Preparation of a Compound of Formula I, Varying m, n, p, A, $R^1$, $R^2$, $R^3$, $R^4$, T, $X^1$, $X^2$, $X^3$, $Y^1$ and $Y^2$ Similarly, following the procedure of 2A above, but optionally replacing amino(iminopentylthiomethyl)-carboxamidine by other compounds of formula (2), and optionally replacing 2-(4-t-butylphenoxy)acetyl chloride with other acid chlorides, the following compounds of Formula I were prepared:

4-methylthio-6-phenyl-1,3,5-triazine-2-ylamine;
4-methylthio-6-(3-trifluoromethylphenyl)-1,3,5-triazine-2-ylamine;
4-methylthio-6-(3-cyanophenyl)-1,3,5-triazine-2-ylamine;
4-methylthio-6-(pyridin-3-yl)-1,3,5-triazine-2-ylamine;
4-methylthio-6-(4-fluorophenyl)-1,3,5-triazine-2-ylamine;
4-methylthio-6-t-butyl-1,3,5-triazine-2-ylamine;
4-methylthio-6-(4-trifluoromethylphenyl)-1,3,5-triazine-2-ylamine;
4-methylthio-6-(phenylthiomethyl)-1,3,5-triazine-2-ylamine;
4-methylthio-6-(2,4-dichlorophenyl)-1,3,5-triazine-2-ylamine;
4-methylthio-6-(4-methylphenyl)-1,3,5-triazine-2-ylamine;
N-(6-{[4-(tert-butyl)phenoxy]methyl}-4-pentylthio-1,3,5-triazine-2-ylamine;
4-methylthio-6-(2-phenylcyclopropyl)-1,3,5-triazine-2-ylamine;
4-methylthio-6-(1-phenoxyethyl)-1,3,5-triazine-2-ylamine;
4-methylthio-6-(2-fluorophenyl)-1,3,5-triazine-2-ylamine;
4-methylthio-6-isopropyl-1,3,5-triazine-2-ylamine;
4-methylthio-6-(4-trifluoromethoxyphenyl)-1,3,5-triazine-2-ylamine;
4-methylthio-6-(1,2-dihydrocyclobut[1,2-a]benzenyl)-1,3,5-triazine-2-ylamine;
4-methylthio-6-(1,2,3,4-tetrahydronaphthyl)-1,3,5-triazine-2-ylamine;
4-methylthio-6-(3-phenylpropyl)-1,3,5-triazine-2-ylamine;
4-methylthio-6-cyclohexyl-1,3,5-triazine-2-ylamine;
4-methylthio-6-(4-dimethylaminophenyl)-1,3,5-triazine-2-ylamine;
4-methylthio-6-(phenoxymethyl)-1,3,5-triazine-2-ylamine;
4-methylthio-6-(4-methoxyphenyl)-1,3,5-triazine-2-ylamine;
4-methylthio-6-(3-fluorophenyl)-1,3,5-triazine-2-ylamine;
4-methylthio-6-(2-phenylethyl)-1,3,5-triazine-2-ylamine;
4-methylthio-6-(4-chlorophenoxy)methyl-1,3,5-triazine-2-ylamine;
4-methylthio-6-(4-methoxymethyl)-1,3,5-triazine-2-ylamine;

4-methylthio-6-(4-trifluorophenoxy)methyl-1,3,5-triazine-2-ylamine;
4-methylthio-6-(4-isopropylphenoxy)methyl-1,3,5-triazine-2-ylamine;
4-methylthio-6-(3-t-butylphenoxy)methyl-1,3,5-triazine-2-ylamine;
4-(t-butylphenyl)methylthio-6-(4-methoxymethyl)-1,3,5-triazine-2-ylamine;
4-(t-butylphenyl)methylthio-6-(4-t-butylphenyl)-1,3,5-triazine-2-ylamine;
4-phenylmethylthio-6-(4-t-butylphenyl)-1,3,5-triazine-2-ylamine;
6-(indan-5-yloxymethyl)-4-methylthio-1,3,5-triazine-2-ylamine;
6-[(3,4-methylenedioxyphenoxy)methyl]-4-methylthio-1,3,5-triazine-2-ylamine;
4-methylthio-6-(3-dimethylaminophenoxy)methyl-1,3,5-triazine-2-ylamine;
4-methylthio-6-(4-acetylphenoxy)methyl-1,3,5-triazine-2-ylamine;
4-methylthio-6-(3-isopropylphenoxy)methyl-1,3,5-triazine-2-ylamine;
6-{[4-t-butylphenyl)thio]methyl}-4-methylthio-1,3,5-triazine-2-ylamine;
4-methylthio-6-(naphth-2-yloxy)methyl-1,3,5-triazine-2-ylamine;
4-methylthio-6-(3-trifluoromethylphenoxy)methyl-1,3,5-triazine-2-ylamine;
4-methylthio-6-[4-(imidazol-1-yl)phenoxy)methyl-1,3,5-triazine-2-ylamine;
N-(6-{[4-(tert-butyl)phenoxy]methyl}-4-ethylthio-1,3,5-triazine-2-ylamine;
N-(6-{[4-(tert-butyl)phenoxy]methyl}-4-propylthio-1,3,5-triazine-2-ylamine;
N-(6-{[4-(tert-butyl)phenoxy]methyl}-4-isopropylthio-1,3,5-triazine-2-ylamine;
N-(6-{[4-(tert-butyl)phenoxy]methyl}-4-n-butylthio-1,3,5-triazine-2-ylamine;
N-(6-{[4-(tert-butyl)phenoxy]methyl}-4-sec butylthio-1,3,5-triazine-2-ylamine;
N-(6-{[4-(tert-butyl)phenoxy]methyl}-4-(3-methylpropyl)thio-1,3,5-triazine-2-ylamine; and
N-(6-{[4-(tert-butyl)phenoxy]methyl}-4-benzylthio-1,3,5-triazine-2-ylamine.

C. Preparation of a Compound of Formula I, Varying m, n, p, A, $R^1$, $R^2$, $R^3$, $R^4$, T, $X^1$, $X^2$, $X^3$, $Y^1$ and $Y^2$ Similarly, following the procedure of 2A above, but optionally replacing amino(iminopentylthiomethyl)-carboxamidine by other compounds of formula (2), and optionally replacing 2-(4-t-butylphenoxy)acetyl chloride with other acid chlorides, the following compounds of Formula I are prepared:

N-(6-{[4-(tert-butyl)phenoxy]methyl}-4-(3-methoxypropyl)thio-1,3,5-triazine-2-ylamine;
N-(6-{[4-(tert-butyl)phenoxy]methyl}-4-(3-hydroxypropyl)thio-1,3,5-triazine-2-ylamine;
N-(6-{[4-(tert-butyl)phenoxy]methyl}-4-cyclopropylthio-1,3,5-triazine-2-ylamine;
N-(6-{[4-(tert-butyl)phenoxy]methyl}-4-(3-methoxypropyl)thio-1,3,5-triazine-2-ylamine;
N-(6-{[4-(tert-butyl)phenoxy]methyl}-4-cyclopentylthio-1,3,5-triazine-2-ylamine;
N-(6-{[4-(tert-butyl)phenoxy]methyl}-4-(cyclopentylmethyl)thio-1,3,5-triazine-2-ylamine;
N-(6-{[4-(tert-butyl)phenoxy]methyl}-4-cyclohexylthio-1,3,5-triazine-2-ylamine;
N-(6-{[4-(tert-butyl)phenoxy]methyl}-4-(thien-2-ylmethyl)thio-1,3,5-triazine-2-ylamine;
N-(6-{[4-(tert-butyl)phenoxy]methyl}-4-(furan-3-yl)thio-1,3,5-triazine-2-ylamine;
N-(6-{[4-(tert-butyl)phenoxy]methyl}-4-(isoxazol-3-ylmethyl)thio-1,3,5-triazine-2-ylamine;
N-(6-{[4-(tert-butyl)phenoxy]methyl}-4-(pyrid-2-yl))thio-1,3,5-triazine-2-ylamine;
N-(6-{[4-(tert-butyl)phenoxy]methyl}-4-[2-(4-chlorophenyl)ethyl]thio-1,3,5-triazine-2-ylamine;
N-(6-{[4-(tert-butyl)phenoxy]methyl}-4-[2-(4-tert-butylphenoxy)ethyl]thio-1,3,5-triazine-2-ylamine;
N-(6-{[4-(tert-butyl)phenoxy]methyl}-4-[2-(4-trifluoromethylphenyl)ethyl]thio-1,3,5-triazine-2-ylamine;
N-(6-{[4-(tert-butyl)phenoxy]methyl}-4-[2-(4-fluorophenoxy)ethyl]thio-1,3,5-triazine-2-ylamine;
N-(6-{[4-(tert-butyl)phenoxy]methyl}-4-[2-(3,5-dichlorophenoxy)ethyl]thio-1,3,5-triazine-2-ylamine;
N-(6-{[4-fluorophenoxy]methyl}-4-methylthio-1,3,5-triazine-2-ylamine;
N-(6-{[4-methylethyl)phenoxy]methyl}-4-methylthio-1,3,5-triazine-2-ylamine;
N-(6-{[3-methoxyhenoxy]methyl}-4-ethylthio-1,3,5-triazine-2-ylamine;
N-(6-{[3,5-dichlorophenoxy]methyl}-4-n-propylthio-1,3,5-triazine-2-ylamine;
N-(6-{2-[4-fluorophenoxy]ethyl}-4-n-butylthio-1,3,5-triazine-2-ylamine;
N-(6-{2-[4-methylethyl)phenoxy]propyl}-4-pentylthio-1,3,5-triazine-2-ylamine;
N-(6-{4-[3-methoxyhenoxy]butyl}-4-pentylthio-1,3,5-triazine-2-ylamine;
N-(6-{1-[3,5-dichlorophenoxy]ethyl}-4-pentylthio-1,3,5-triazine-2-ylamine;
N-(6-[(pyrid-2-yl)methyl]-4-pentylthio-1,3,5-triazine-2-ylamine;
N-(6-(cyclohexylmethyl)-4-pentylthio-1,3,5-triazine-2-ylamine;
N-(6-[(2-hydroxycyclopentyl)methyl]-4-pentylthio-1,3,5-triazine-2-ylamine; and
N-(6-(furan-3-ylmethyl)-4-pentylthio-1,3,5-triazine-2-ylamine.

EXAMPLE 3

Preparation of a Compound of Formula (3)

A. Preparation of a Compound of Formula (3) in which $R^4$ is Methyl

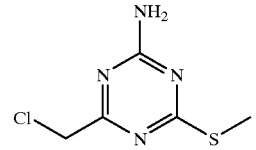

To a suspension of 2-imino-4-thiobiurea (3 g, 25.4 mmole) in dry tetrahydrofuran (100 ml) iodomethane (1.9 mL, 30.4 mmole) was added and stirred at room temperature for 16 hours. To the resulting solution was added a solution of chloroacetyl chloride in anhydrous tetrahydrofuran (25 ml), followed by anhydrous N, N-diisopropylethylamine (9.75 mL, 56 mmole), and the mixture stirred at room temperature for 16 hours. The reaction mixture was concentrated under reduced pressure and the residue dissolved in ethyl acetate (150 mL) and washed with water (3×50 mL), 10% NaOH (2×25 mL), brine (1×50) and dried over anhydrous sodium sulfate. The solvent was removed under reduced pressure and the residue purified on silica gel using a hexane/ethyl acetate gradient (10% to 40% ethyl acetate) to give 6-(chloromethyl-4-methylthio-1,3,5-triazine-2-ylamine, a compound of formula (3).

B. Preparation of a Compound of Formula (3), Varying $R^4$

Similarly, following the procedure of 3A above, but replacing iodomethane by other compounds of formula $R^4Hal$, other compounds of formula (3) are prepared in which $R^4$ is ethyl, n-propyl, isopropyl, n-butyl, sec-butyl, t-butyl, n-pentyl, benzyl, and 4-t-butylbenzyl.

EXAMPLE 4

Preparation of a Compound of Formula I

A. Preparation of a Compound of Formula I in which $R^1$ and $R^2$ are Hydrogen, $R^3$ is 3-Chlorophenyl, $R^4$ is Methyl, T is —NH—, A is a Covalent Bond, $X^1$, $X^2$, and $X^3$ are All Nitrogen m is 0, n is 1 and $Y^2$ is Methylene, and Z is Sulfur.

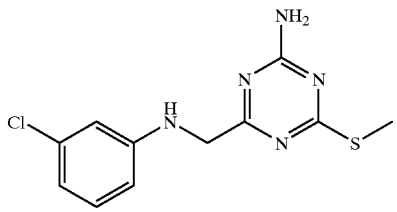

To a solution of 6-(chloromethyl-4-methylthio-1,3,5-triazine-2-ylamine (75 mg, 0.39 mmol) in dry tetrahydrofuran (3 mL) was added a solution of 3-chloroaniline (0.210 mL, 1.97 mmol) in dry tetrahydrofuran (1 mL) followed by anhydrous N,N-diisopropylethylamine (0.343 mL, 1.95 mmol). The mixture was heated under reflux for 16 hours, after which the solvent was evaporated. The residue was purified by reverse phase HPLC to give 4-[(3-chlorophenylamino)methyl]-6-methylthio-[1,3,5]triazin-2-ylamine. M+1=266.1.

B. Preparation of a Compound of Formula I, in which T is —$NR^5$—, Varying A, m, n, p, $R^1$, $R^3$, $R^4$, $X^1$, $X^2$, $X^3$, $Y^1$ and $Y^2$ Similarly, following the procedure of 4A above, but optionally replacing 6-(chloromethyl-4-methylthio-1,3,5-triazine-2-ylamine by other compounds of formula (3), and optionally replacing 3-chloroaniline with other amines of formula $R^3(Y^1)_nR^5NH$, the following compounds of Formula I were prepared where T is: —$NR^5$—;

4-methylthio-6-[4-(1,1,1,3,3,3-hexafluoropropan-2-ol)phenylaminomethyl]-1,3,5-triazine-2-ylamine;
4-methylthio-6-[(dicyclohexylamino)methyl]-1,3,5-triazine-2-ylamine;
4-methylthio-6-[(dibenzylamino)methyl]-1,3,5-triazine-2-ylamine;
4-methylthio-6-[(benzylisopropylamino)methyl]-1,3,5-triazine-2-ylamine;
4-methylthio-6-[(4-(pyrimidin-2-yl)piperazin-1-yl)methyl]-1,3,5-triazine-2-ylamine;
6-[4-(3,4-methylenedioxyphenyl)piperazin-1-yl)methyl]-4-methylthio-1,3,5-triazine-2-ylamine;
6-{[4-((2E)-3-phenylprop-2-enyl)piperazin-1-yl)methyl]-4-methylthio-1,3,5-triazine-2-ylamine;
4-methylthio-6-[(2,6-dimethylphenyl)aminomethyl]-1,3,5-triazine-2-ylamine;
4-methylthio-6-[(3-chlorophenyl)aminomethyl]-1,3,5-triazine-2-ylamine;
6-[(4-methylpiperazin-1-yl)methyl]-4-methylthio-1,3,5-triazine-2-ylamine;
6-[(4-(3,4-dimethylphenyl)piperazin-1-yl)methyl]-4-methylthio-1,3,5-triazine-2-ylamine;
6-[(4-(2-fluorophenyl)piperazin-1-yl)methyl]-4-methylthio-1,3,5-triazine-2-ylamine;
4-methylthio-6-[(4-piperidylpiperidyl)methyl]-1,3,5-triazine-2-ylamine;
N-{[(3,5-dimethoxyphenyl]aminomethyl}-4-methylthio-1,3,5-triazine-2-ylamine;
N-{[(4-chlorophenyl]aminomethyl}-4-methylthio-1,3,5-triazine-2-ylamine;
6-[4-(4-methylpiperidyl)methyl]-4-methylthio-1,3,5-triazine-2-ylamine;
6-[4-(4-fluorophenyl)piperazin-1-yl)methyl]-4-methylthio-1,3,5-triazine-2-ylamine; and
4-methylthio-6-[(2,4-dimethoxyphenyl)aminomethyl]-1,3,5-triazine-2-ylamine.

C. Preparation of a Compound of Formula I, in which T is —$NR^5$—, Varying A, m, n, p, $R^1$, $R^2$, $R^3$, $R^4$, $X^1$, $X^2$, $X^3$, $Y^1$ and $Y^2$ Similarly, following the procedure of 3A above, but optionally replacing 6-(chloromethyl-4-methylthio-1,3,5-triazine-2-ylamine by other compounds of formula (3), and optionally replacing 3-chloroaniline with other amines of formula $R^3(Y^1)_nR^5NH$, the following compounds of Formula I where T is: —$NR^5$— are prepared;

4-[(3-chlorophenylamino)methyl]-6-pentylthio-[1,3,5]triazin-2-ylamine;
4-[(3-chlorophenylamino)methyl]-6-(3-methoxypropyl)thio-[1,3,5]triazin-2-ylamine;
4-[(3-chlorophenylamino)methyl]-6-(3-hydroxypropyl)thio-[1,3,5]triazin-2-ylamine;
4-[(3-chlorophenylamino)methyl]-6-cyclopropylthio-[1,3,5]triazin-2-ylamine;
4-[(3-chlorophenylamino)methyl]-6-cyclopentylthio-[1,3,5]triazin-2-ylamine;
4-[(3-chlorophenylamino)methyl]-6-(cyclopentylmethyl)thio-[1,3,5]triazin-2-ylamine;
4-[(3-chlorophenylamino)methyl]-6-(thien-2-yl)thio-[1,3,5]triazin-2-ylamine;
4-[(3-chlorophenylamino)methyl]-6-(furan-3-yl)thio-[1,3,5]triazin-2-ylamine;
4-[(3-chlorophenylamino)methyl]-6-(isoxazol-3-ylmethyl)thio-[1,3,5]triazin-2-ylamine;
4-[(3-chlorophenylamino)methyl]-6-(pyrid-2-yl)thio-[1,3,5]triazin-2-ylamine;
4-[(3-chlorophenylamino)methyl]-6-[2-(4-chlorophenyl)ethyl]thio-[1,3,5]triazin-2-ylamine;
4-[(3-chlorophenylamino)methyl]-6-[2-(4-tert-butylphenoxy)ethyl]thio-[1,3,5]triazin-2-ylamine;
4-[(3-chlorophenylamino)methyl]-6-[2-(4-trifluoromethylphenyl)ethyl]thio-[1,3,5]triazin-2-ylamine;
4-[(3-chlorophenylamino)methyl]-6-[2-(4-fluorophenoxy)ethyl]thio-[1,3,5]triazin-2-ylamine;
4-[(3-chlorophenylamino)methyl]-6-[2-(3,5-dichlorophenoxy)ethyl]thio-[1,3,5]triazin-2-ylamine;
4-[(4-fluorophenylamino)methyl]-6-pentylthio-[1,3,5]triazin-2-ylamine;
4-[(4-methylethylphenylamino)methyl]-6-pentylthio-[1,3,5]triazin-2-ylamine;
4-[(4-methoxyphenylamino)methyl]-6-pentylthio-[1,3,5]triazin-2-ylamine;
4-[(3,5-dichlorophenylamino)methyl]-6-pentylthio-[1,3,5]triazin-2-ylamine;
4-[(3-chlorophenylamino)methyl]-6-n-butylthio-[1,3,5]tazin-2-ylamine;

4-[(3-methoxyphenylamino)methyl]-6-n-pentylthio-[1,3,5]
triazin-2-ylamine;

4-[2-(3,5-dichlorophenylamino)ethyl]-6-n-pentylthio-[1,3,
5]triazin-2-ylamine;

4-[(pyrid-2-ylamino)methyl]-6-n-pentylthio-[1,3,5]triazin-
2-ylamine;

4-[(cyclohexylamino)methyl]-6-n-pentylthio-[1,3,5]triazin-
2-ylamine;

4-[(2-hydroxycyclopentyl)aminomethyl]-6-n-pentylthio-[1,
3,5]triazin-2-ylamine; and 4-[(furan-3-ylamino)methyl]-6-n-butylthio-[1,3,5]triazin-2-
ylamine.

EXAMPLE 5

Preparation of a Compound of Formula I

A. Preparation of a Compound of Formula I in which $R^1$ is 2-Thienyl, $R^2$ is Hydrogen, $R^3$ is 4-Tert-butylphenyl, $R^4$ is Methyl, T is Oxygen-, A is —C($Z^1$), $Z^1$ is Oxygen, $X^1$, $X^2$, and $X^3$ are All Nitrogen, m is 0, n is 1, $Y^2$ is Methylene and p is 1, and Z is Sulfur.

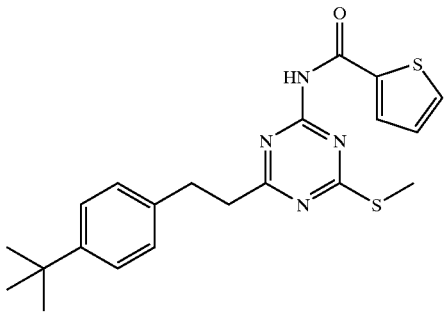

To a solution of 6-{[4-(tert-butyl)phenoxy]methyl-4-methylthio-1,3,5-triazine-2-ylamine, a compound of Formula I where A is a covalent bond and $R^1$ and $R^2$ are both hydrogen (25 mg, 0.082 mmol), in dry tetrahydrofuran (5 mL) under nitrogen, sodium hydride (5.76 mg, 0.24 mmol) was added and stirred at room temperature for 1 hour. To the resulting suspension a solution of 2-thiophene-2-carbonyl chloride (0.009 mL, 0.082 mmol) in dry tetrahydrofuran (1 mL) was added and the reaction mixture was stirred at room temperature for 16 hours. The reaction was quenched with water and the mixture was purified by reverse phase HPLC to give N-(6-{[4-(tert-butyl)phenoxy]methyl-4-methylthio-1,3,5-triazine-2-thienylcarboxamide, M+1=415.1.

B. Preparation of a Compound of Formula I in which $R^1$ is Allyl, R2 is Hydrogen, $R^3$ is 4-Tert-butylphenyl, $R^4$ is Methyl, T is Oxygen-, A is —C($Z^1$), $Z^1$ is Oxygen, $X^1$, $X^2$, and $X^3$ are All Nitrogen, m is 0, n is 1, $Y^2$ is Methylene and p is 1, and Z is Sulfur.

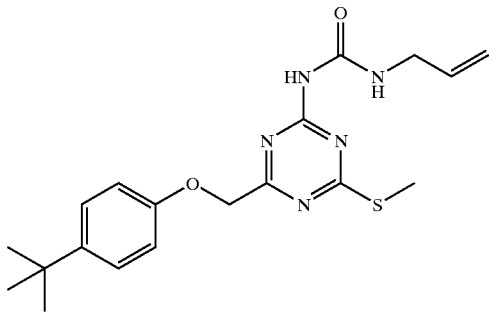

To a solution of 6-{[4-(tert-butyl)phenoxy]methyl-4-methylthio-1,3,5-triazine-2-ylamine (100 mg, 0.328 mmol) in dry tetrahydrofuran (5 mL), under nitrogen, at 0° C. allyl isocyanate (0.028 mL, 0.3285 mmol) was added in drops and the mixture was allowed to warm up to room temperature over 16 hours. Solvent was evaporated and the mixture was purified by reverse phase HPLC to give N-(6-{[4-(tert-butyl)phenoxy]methyl-4-methylthio-1,3,5-triazin-2-yl)(prop-2-enylamino)carboxamide. M+1=388.1.

C. Preparation of a Compound of Formula I in which $R^1$ is Benzyl, $R^2$ is Hydrogen, $R^3$ is 4-Tert-butylphenyl, $R^4$ is Methyl, T is Oxygen-, A is a Covalent Bond, $X^1$, $X^2$, and $X^3$ are All Nitrogen, m is 0, n is 1 $Y^2$ is Methylene and p is 1, and Z is Sulfur.

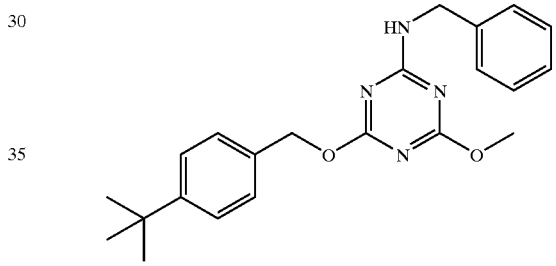

a) Cyanuric chloride (0.75 g, 4.07 mmol) was dissolved in dry $CH_2Cl_2$ (10 ml) and cooled to 0° C. To the solution was added diisopropylethylamine (777 μl, 4.47 mmol) followed by drop wise addition of benzylamine (444 μl, 4.07 mmol). The cooled solution was stirred for 2 hours at 0° C. and allowed to warm to room temperature overnight. The reaction mixture was concentrated under reduced pressure to provide (4,6-dichloro(1,3,5-triazin-2-yl)benzylamine, which used in the next step without further purification.

b) The product from the above reaction was dissolved in methanol, followed by addition of solid sodium methoxide (1 equiv.), and the mixture was stirred overnight at room temperature. The reaction was concentrated under reduced pressure, dissolved in $CH_2Cl_2$, washed with water, brine, and dried over sodium sulphate. The solvent was removed and the residue was purified on silica gel (100% hexane to 1:1 hexane:EtOAc), to provide 6-chloro-4-methoxy(1,3,5-triazin-2-yl)benzylamine.

c) Sodium hydride (36.7 mg, 0.937 mmol) was suspended in dry DMF (10 ml) followed by addition of 4-tert-butylbenzyl alcohol (111 μl, 0.625 mmol) and stirred for 30 minutes. The product from b) (100 mg 0.398 mmol) was dissolved in dry DMF (1 ml) and added to the benzyl alcohol solution. The reaction was allowed to stir at room temperature for 2 hours, followed by heating to 90° C. overnight. The reaction was cooled, diluted with water (30 ml) and extracted with ethyl acetate. The organic fractions were combined and washed with water, brine, dried over sodium sulphate and concentrated under reduced pressure. The residue was purified by reverse phase HPLC to give the desired product, (6-{[4-(4-tert-butylphenyl]methoxy(1,3,5-triazin-2-yl)}benzylamine.

D. Similarly, following the procedure of 5A, 5B, or 5C above, but optionally replacing 6-{[4-(tert-butyl)phenoxy]methyl-4-methylthio-1,3,5-triazine-2-ylamine by other compounds of Formula I in which $R^1$ and $R^2$ are hydrogen and A is a covalent bond, and optionally replacing 2-thiophene-2-carbonyl chloride, allyl isocyanate, and benzyl bromide with other compounds of formula $R^1C((O)Cl$, $R^1NCO$, and $R^1Halo$, the following compounds of Formula I were prepared;

N-(6-{[4-(tert-butyl)phenoxy]methyl}-4-methylthio-(1,3,5-triazine-2-yl))(4-chlorophenyl)carboxamide;
N-(6-{[4-(tert-butyl)phenoxy]methyl}-4-methylthio-(1,3,5-triazine-2-yl))(phenylamino)carboxamide;
N-(6-{[4-(tert-butyl)phenoxy]methyl}-4-methylthio-(1,3,5-triazine-2-yl))(4-methoxyphenyl)carboxamide;
N-(6-{[4-(tert-butyl)phenoxy]methyl}-4-methylthio-(1,3,5-triazine-2-yl))(4-dimethylaminophenyl)carboxamide;
N-(6-{[4-(tert-butyl)phenoxy]methyl}-4-methylthio-(1,3,5-triazine-2-yl))(ethylamino)carboxamide;
N-(6-{[4-(tert-butyl)phenoxy]methyl}-4-methylthio-(1,3,5-triazine-2-yl))-2, 2-dimethylpropanamido;
N-(6-{[4-(tert-butyl)phenoxy]methyl}-4-methylthio-(1,3,5-triazine-2-yl))(cyclohexylamino)carboxamide;
N-(6-{[4-(tert-butyl)phenoxy]methyl}-4-methylthio-(1,3,5-triazine-2-yl))(methylethylamino)carboxamide;
N-(6-{[4-(tert-butyl)phenoxy]methyl}-4-methylthio-(1,3,5-triazine-2-yl))(prop-2-enylamino)carboxamide;
N-(6-[4-(tert-butyl)phenyl]-4-methylthio-1,3,5-triazine-2-yl)amine;
N-(6-[4-(tert-butyl)phenylmethoxy)-4-methylthio-(1,3,5-triazine-2-yl)benzylamine;
(4-amino-6-methylthio(1,3,5-triazin-2-yl)methyl][2-(diethylamino)-ethyl]ethylamine
N-[4-methylthio-6-(2-phenylcyclopropyl(1,3,5-triazine-2-yl)}(2-phenylcyclopropyl)carboxamide; and
N-(4-amino-6-methylthio(1,3,5-triazine-2-yl))[4-t-butylphenyl]carboxamide.

E. Similarly, following the procedure of 5A, 5B, or 5C above, but optionally replacing 6-{[4-(tert-butyl)phenoxy]methyl-4-methylthio-1,3,5-triazine-2-ylamine by other compounds of Formula I in which $R^1$ and $R^2$ are hydrogen and A is a covalent bond, and optionally replacing 2-thiophene-2-carbonyl chloride, allyl isocyanate, and benzyl bromide with other compounds of formula $R^1C((O)Cl$, $R^1NCO$, and $R^1Halo$, the following compounds of Formula I are prepared;

N-(6-{[4-(tert-butyl)phenoxy]methyl-4-methylthio-1,3,5-triazine-2-thienylthiocarboxamide;
N-(6-{[4-(tert-butyl)phenoxy]methyl-4-methylthio-(1,3,5-triazine-2-yl)benzamide;
N-(6-{[4-(tert-butyl)phenoxy]methyl-4-methylthio-(1,3,5-triazine-3-furanylcarboxamide;
N-(6-{[4-(tert-butyl)phenoxy]methyl-4-methylthio-(1,3,5-triazine-2-thienylcarboxamide
N-(6-{[4-(tert-butyl)phenoxy]methyl}-4-(3-methoxypropyl)thio-1,3,5-triazine-2-thienylcarboxamide;
N-(6-{[4-(tert-butyl)phenoxy]methyl}-4-(3-hydroxypropyl)thio-1,3,5-triazine-2-thienylcarboxamide;
N-(6-{[4-(tert-butyl)phenoxy]methyl}-4-cyclopropylthio-1,3,5-triazine-2-thienylcarboxamide;
N-(6-{[4-(tert-butyl)phenoxy]methyl}-4-(3-methoxypropyl)thio-1,3,5-triazine-2-thienylcarboxamide;
N-(6-{[4-(tert-butyl)phenoxy]methyl}-4-cyclopentylthio-1,3,5-triazine-2-thienylcarboxamide;
N-(6-{[4-(tert-butyl)phenoxy]methyl}-4-(cyclopentylmethyl)thio-1,3,5-triazine-2-thienylcarboxamide;
N-(6-{[4-(tert-butyl)phenoxy]methyl-4-cyclohexylthio-1,3,5-triazine-2-thienylcarboxamide;
N-(6-{[4-(tert-butyl)phenoxy]methyl}-4-(thien-2-ylmethyl)thio-1,3,5-triazine-2-thienylcarboxamide;
N-(6-{[4-(tert-butyl)phenoxy]methyl}-4-(furan-3-yl)thio-1,3,5-triazine-2-thienylcarboxamide;
N-(6-{[4-(tert-butyl)phenoxy]methyl}-4-(isoxazol-3-ylmethyl)thio-1,3,5-triazine-2-thienylcarboxamide;
N-(6-{[4-(tert-butyl)phenoxy]methyl}-4-(pyrid-2-yl))thio-1,3,5-triazine-2-thienylcarboxamide;
N-(6-{[4-(tert-butyl)phenoxy]methyl}-4-[2-(4-chlorophenyl)ethyl]thio-1,3,5-triazine-2-thienylcarboxamide;
N-(6-{[4-(tert-butyl)phenoxy]methyl}-4-[2-(4-tert-butylphenoxy)ethyl]thio-1,3,5-triazine-2-thienylcarboxamide;
N-(6-{[4-(tert-butyl)phenoxy]methyl}-4-[2-(4-trifluoromethylphenyl)ethyl]thio-1,3,5-triazine-2-thienylcarboxamide;
N-(6-{[4-(tert-butyl)phenoxy]methyl}-4-[2-(4-fluorophenoxy)ethyl]thio-1,3,5-triazine-2-thienylcarboxamide;
N-(6-{[4-(tert-butyl)phenoxy]methyl}-4-[2-(3,5-dichlorophenoxy)ethyl]thio-1,3,5-triazine-2-thienylcarboxamide;
N-(6-{[4-fluorophenoxy]methyl}-4-methylthio-1,3,5-triazine-2-thienylcarboxamide;
N-(6-{[4-methylethyl)phenoxy]methyl}-4-methylthio-1,3,5-triazine-2-thienylcarboxamide;
N-(6-{[3-methoxyhenoxy]methyl}-4-ethylthio-1,3,5-triazine-2-thienylcarboxamide;
N-(6-{[3,5-dichlorophenoxy]methyl}-4-n-propylthio-1,3,5-triazine-2-thienylcarboxamide;
N-(6-{2-[4-fluorophenoxy]ethyl}-4-n-butylthio-1,3,5-triazine-2-thienylcarboxamide;
N-(6-{2-[4-methylethyl)phenoxy]propyl}-4-pentylthio-1,3,5-triazine-2-thienylcarboxamide;
N-(6-{4-[3-methoxyhenoxy]butyl}-4-pentylthio-1,3,5-triazine-2-thienylcarboxamide;
N-(6-{1-[3,5-dichlorophenoxy]ethyl}-4-pentylthio-1,3,5-triazine-2-thienylcarboxamide;
N-(6-[(pyrid-2-yl)methyl]-4-pentylthio-1,3,5-triazine-2-thienylcarboxamide;
N-(6-(cyclohexylmethyl)-4-pentylthio-1,3,5-triazine-2-thienylcarboxamide;
N-(6-[(2-hydroxycyclopentyl)methyl]-4-pentylthio-1,3,5-triazine-2-thienylcarboxamide;
N-(6-(furan-3-ylmethyl)-4-pentylthio-1,3,5-triazine-2-thienylcarboxamide;
4-[(3-chlorophenylamino)methyl]-6-methylthio-[1,3,5]triazin-2-thienylcarboxamide;
N-(6-{[4-(tert-butyl)phenoxy]methyl-4-methylthio-(1,3,5-triazine-2-yl)(butylamino)carboxamide;
N-(6-{[4-(tert-butyl)phenoxy]methyl-4-methylthio-(1,3,5-triazine-2-yl)(pentylamino)carboxamide;
N-(6-{[4-(tert-butyl)phenoxy]methyl-4-methylthio-(1,3,5-triazine-2-yl)(cyclohexylamino)carboxamide;
N-(6-{[4-(tert-butyl)phenoxy]methyl-4-methylthio-(1,3,5-triazine-2-yl)(3-hydroxypentylamino)carboxamide;
N-(6-{[4-(tert-butyl)phenoxy]methyl-4-methylthio-(1,3,5-triazine-2-yl)(but-2-enylamino)carboxamide;
N-(6-{[4-(tert-butyl)phenoxy]methyl-4-methylthio-(1,3,5-triazine-2-yl)(furan-3-ylamino)carboxamide;

N-(6-{[4-(tert-butyl)phenoxy]methyl-4-methylthio-(1,3,5-triazine-2-yl)(phenylamino)carboxamide;
N-(6-{[4-(tert-butyl)phenoxy]methyl-4-methylthio-(1,3,5-triazine-2-yl)(4-fluorophenylamino)carboxamide;
N-(6-{[4-(tert-butyl)phenoxy]methyl-4-methylthio-(1,3,5-triazine-2-yl)(pyrid-4-ylamino)carboxamide;
N-(6-{[4-(tert-butyl)phenoxy]methyl}-4-(3-methoxypropyl)thio-(1,3,5-triazine-2-yl)(ethylamino)carboxamide;
N-(6-{[4-(tert-butyl)phenoxy]methyl}-4-(3-methoxypropyl)thio-(1,3,5-triazine-2-yl)(ethylamino)carboxamide;
N-(6-{[4-(tert-butyl)phenoxy]methyl}-4-cyclopentylthio-(1,3,5-triazine-2-yl)(ethylamino)carboxamide;
N-(6-{[4-(tert-butyl)phenoxy]methyl}-4-(thien-2-ylmethyl)thio-(1,3,5-triazine-2-yl)(ethylamino)carboxamide;
N-(6-{[4-(tert-butyl)phenoxy]methyl}-4-(furan-3-yl)thio-(1,3,5-triazine-2-yl)(isopropylamino)carboxamide;
N-(6-{[4-(tert-butyl)phenoxy]methyl}-4-(pyrid-2-yl))thio-1,3,5-triazine-2-ylamine;
N-(6-{[4-(tert-butyl)phenoxy]methyl}-4-[2-(4-chlorophenyl)ethyl]thio-(1,3,5-triazine-2-yl)(prop-2-enylamino)carboxamide;
N-(6-{[4-(tert-butyl)phenoxy]methyl)-4-[2-(4-tert-butylphenoxy)ethyl]thio-(1,3,5-triazine-2-yl)(ethylamino)carboxamide;
N-(6-{[4-fluorophenoxy]methyl}-4-methylthio-(1,3,5-triazine-2-yl)(ethylamino)carboxamide;
N-(6-{2-[4-methylethyl)phenoxy]propyl}-4-pentylthio-(1,3,5-triazine-2-yl)(ethylamino)carboxamide;
N-(6-[(pyrid-2-yl)methyl]-4-pentylthio-(1,3,5-triazine-2-yl)(ethylamino)carboxamide;
N-(6-(furan-3-ylmethyl)-4-pentylthio-N-(6-(cyclohexylmethyl)-4-pentylthio-1,3,5-triazine-2-ylamine;
N-(6-[(2-hydroxycyclopentyl)methyl]-4-pentylthio-1,3,5-triazine-2-ylamine;

EXAMPLE 6

Preparation of a Compound of Formula I

A. Preparation of a Compound of Formula I in which $R^1$ and $R^2$ are Hydrogen $R^3$ is 4-Tert-butylphenyl $R^4$ is Methyl, $(T)_n$ is NH, A is a Covalent Bond, $X^2$ and $X^3$ are Nitrogen, $X^3$ is CH, $Y^1$ is —C(O)— and m is 1, n is 1, p is 0, and Z is Sulfur

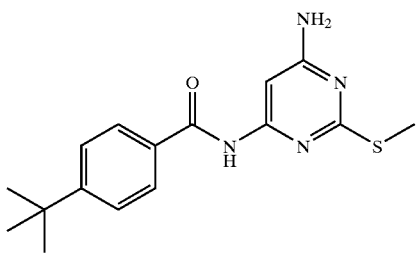

To a solution of 4,6-diamino-2-methylmercaptopyrimidine (50 mg, 0.032 mmol) in anhydrous tetrahydrofuran was added sodium hydride, followed by the addition of 4-t-butylbenzoyl chloride (0.084 mL, 0.32 mmol) and N, N-diisopropylethylamine. The mixture was heated at 50° C. for 16 hours after which it was subjected to aqueous work up. The product was extracted with ethyl acetate and purified by HPLC to give N-(6-amino-2-methylthiopyrimidin-4-yl)[4-(tert-butyl)phenyl] carboxamide. M+1=317.3.

B. Preparation of a Compound of Formula I in which $X^2$ and $X^3$ are Nitrogen and $X^3$ is CH, Varying A, m, n, $R^1$, $R^2$, $R^3$, $R^4$, A, $(T)_n$, $(Y^1)_n$, $(Y^2)_n$, and Z Similarly, following the procedure of 6A above, but optionally replacing 4,6-diamino-2-methylmercaptopyrimidine by other compounds of formula (4), and optionally replacing 4-t-butylbenzoyl chloride with other compounds of formula R1-$(Y^1)_n$-Halo the following compounds of Formula I are prepared;

N-(6-amino-2-ethylthiopyrimidin-4-yl)[4-(tert-butyl)phenyl]carboxamide;
N-(6-amino-2-isopropylthiopyrimidin-4-yl)[4-(tert-butyl)phenyl]carboxamide;
N-(6-amino-2-isopropylthiopyrimidin-4-yl)[4-(tert-butyl)phenyl]carboxamide;
N-(6-amino-2-cyclopentylthiopyrimidin-4-yl)[4-(tert-butyl)phenyl]-(ethylamino)carboxamide; and
N-(6-amino-2-isopropylthiopyrimidin-4-yl)[4-(tert-butyl)phenyl](2-thienyl)carboxamide.

The following examples illustrate the preparation of representative pharmaceutical formulations containing a compound of Formula I.

EXAMPLE 7

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 8

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 9

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 10

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 11

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 12

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 13

A subcutaneous formulation may be prepared as follows:

| Ingredient | Quantity |
|---|---|
| Active Ingredient | 5.0 mg |
| Corn Oil | 1.0 mL |

EXAMPLE 14

An injectable preparation is prepared having the following composition:

| Ingredients | Amount |
|---|---|
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 15

A topical preparation is prepared having the following composition:

| Ingredients | grams |
|---|---|
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 16

| | Sustained Release Composition | | |
|---|---|---|---|
| Ingredient | Weight Range (%) | Preferred Range (%) | Most Preferred |
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |

-continued

Sustained Release Composition

| Ingredient | Weight Range (%) | Preferred Range (%) | Most Preferred |
|---|---|---|---|
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl, methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 17 pGL3 Luciferase Assay

This example shows the effect of the compounds of the invention on ABCA-1 gene expression, using the pGL3 luciferase reporter vector system (Promega, Madison, Wis.) to create a recombinant plasmid to measure reporter gene expression under control of the ABCA-1 promoter.

Construction of Reporter Plasmids:

Plasmid pGL3-Basic (Promega, Madison, Wis.; Cat. #E1751) was used as a control plasmid containing the promoterless luciferase gene. The reporter construct containing the ABCA-1 promoter and luciferase gene was made by cloning a genomic fragment from the 5' flanking region of the ABCA-1 gene (hAPRI 5' promoter, corresponding to nucleotides 1080–1643 of SEQ ID NO: 3) into the SacI site of the GL3-Basic plasmid to generate plasmid GL-6a. Next, plasmid GL-6a was digested with SpeI and Acc65I. A BsiWI-SpeI fragment excised from a lambda subclone, representing the ABCA-1 genomic sequence corresponding to nucleotides 1–1534 of SEQ ID NO: 3 was ligated into the remaining vector/ABCA-1 promoter fragment produced by this digestion. The resultant plasmid, pAPR1, encodes the luciferase reporter gene under transcriptional control of 1.75 kb of the human ABCA-1 promoter sequence.

Transfection of Reporter Constructs: The above-described control or pAPR1 plasmid was transfected into confluent cultures of RAW 264.7 cells maintained in DMEM containing 10% fetal bovine serum. Each well of a 12 well dish was transfected for 5 hours with either pGL3-Basic, pGL3-Promoter or pAPR1 DNA (1 $\mu$g), luciferase plasmid DNA (1 $\mu$g), and 12 $\mu$l of Geneporter reagent (Gene Therapy Systems, San Diego, Calif.; Cat. #T201007). In addition, 0.1 $\mu$g of pCMV$\beta$ plasmid DNA (Clontech, Palo Alto, Calif., Cat. #6177-1) was added as a control for transfection efficiency. After 5 hours, the culture medium was replaced with serum-free DMEM/BSA in the presence of or absence of acetylated LDL (100 $\mu$g/ml) and incubated for 24 hours.

For added convenience in high throughput screening, cultured cells can be stably transfected with reporter plasmids using the following procedure. First, 5×10$^6$ RAW 264.7 cells are transfected for 5 hours in a 60 mm dish with 9 $\mu$g of the pAPR1 plasmid and pCMVscript (Stratagene, LaJolla, Calif.) in 10 ml of serum-free DMEM with 50 $\mu$l Geneporter transfection reagent (Gene Therapy Systems, San Diego, Calif.). Subsequently, the transfection medium is replaced with complete medium and the cells incubated overnight at 37° C. Subsequently, the cells are transferred to separate dishes at dilutions ranging from 1:5 to 1:1000 and incubated in selection medium containing 800 $\mu$g/ml G418 (Life Technologies, Bethesda, Md.) for 20 days. Visible colonies are picked, expanded, and assayed for luciferase activity as described below. Using this method, five clonal cell lines positive for luciferase activity were identified for use in high throughput assays.

Luciferase Assay: Following transfection, the cells in each well were lysed in 70 $\mu$l of 1× cell lysis reagent (Promega, Madison, Wis., Cat. #E3971), subjected to one freeze-thaw cycle, and the lysate cleared by centrifugation for 5 minutes at 12,000 g. After centrifugation, 100 $\mu$l of luciferase assay reagent (Promega, Madison, Wis.; Cat. #E1501) was added to 10 $\mu$l of lysate. The luciferase activity of each lysate was measured as light units using a luminometer. Additionally, the $\beta$-galactosidase activity of each lysate was measured using the chemiluminescent assay reagents supplied in the Galacto-light kit according to the manufacturer's instructions (Tropix Inc., Bedford, Mass.: Cat. #BL100G). The normalized luciferase activity for each lysate was determined by dividing the luciferase activity value by the determined $\beta$-galactosidase value and reported as relative light units.

The compounds of the invention demonstrated increased ABCA-1 gene expression in this assay.

EXAMPLE 18 mRNA Assays

Modulation of expression of ABCA-1 mRNA levels by the compounds of the invention were determined in the following assays.

Quantitative PCR

Cultures of THP were grown to subconfluence in DMEM/ 10% FBS before replacement with DMEM/BSA and the indicated additive for 24 or 48 hours. RNA using standard methods.

Quantitative PCR was carried out using the GeneAmp 5700 Sequence Detection System (Perkin-Elmer Applied Biosystems, Foster City, Calif.). Briefly, 500 ng of DNAse—treated mRNA was reverse transcribed using random hexamer primers at 2.5 µM. Approximately 5% of this reaction was amplified by PCR using the SYBR green core kit (PE Applied Biosystems, Foster City, Calif.; Cat. #4304886) and human ABCA-1 primers LF:5'-CCTCTCATTACACAAAAACCAGAC (SEQ ID NO: 11) and LR:5'-GCTTTCTTTCACTTCTCATCCTG (SEQ ID NO: 12) to yield an 82 bp fragment corresponding to nucleotides 7018–7099 of human ABCA-1. PCR cycle conditions were as follows: 10 minutes 95° C.; followed by 40 cycles of 95° C., 15 seconds; and 60° C., 60 seconds. The mRNA in each sample was quantitated by detecting the increase in fluorescence caused by SYBR green binding to the double-stranded amplification product generated during each PCR cycle. All samples were run in triplicate and normalized against P-actin mRNA, amplified in parallel reactions with primers actin F:5'-TCACCCACACTGTGCCATCTACGA (SEQ ID NO: 54) and actin B:5'-CAGCGGAACCGCTCATTGCCAATGG (SEQ ID NO: 55). Standard curves were run for both ABCA-1 and β-actin on the same PCR plate.

Changes in mRNA levels were also determined using RAW 264.7 cells with a QuantiGene® Expression Kit from Bayer.

The compounds of the invention modulated expression of ABCA-1 mRNA levels in this assay.

EXAMPLE 19

Lipid Efflux Assay

This example demonstrates that enhanced expression of ABCA-1 protein in the plasma membrane is associated with lipid efflux.

Cell-surface labeling and immunoprecipitation is used to determine whether increased expression of ABCA-1 protein in the plasma membrane is correlated with an increase in cholesterol efflux. The relative amount of ABCA-1 on the cell surface is determined by cross-linking surface proteins on intact cells with the membrane-impermeable agent sulfo-NHS-biotin, followed by the steps of membrane solubilization, immunoprecipitation with ABC1 antibody, SDS-PAGE, and detection with streptavidin.

Cell Culture: Fibroblasts are cultured under control conditions and conditions known to increase cholesterol efflux (Oram, et al., J. Lip. Res., 40: 1769–1781 (1999)). Control cells are grown to confluence in DMEM/10% FBS and then incubated in DMEM/BSA for 18 hours with no additives (control). cAMP-treated cells are grown to confluence in DMEM/10% FBS and then incubated in DMEM/BSA for 18 hours with 1 mM 8-Br-cAMP(cAMP). Cholesterol-loaded cells are grown to confluence in DMEM/10% FBS and then incubated in DMEM/BSA for 48 hours with 30 µg/ml cholesterol plus 18 hours with no additives (cholesterol). Cholesterol-loaded cells treated with cAMP are grown to confluence in DMEM/10% FBS and then incubated in DMEM/BSA for 48 hours with 30 µg/ml cholesterol plus 18 hours with 1 mM 8-Br-cAMP (cholesterol+cAMP).

Cell-surface Labeling: For selective labeling of plasma membrane ABCA-1, the cells are incubated for 30 minutes at 0° C. with PBS containing 1 mg/ml sulfo-NHS-biotin (Pierce, Rockford, Ill.; Cat. #21217) to biotinylate cell-surface proteins (see Walker et al., Biochemistry, 50:14009–14014 (1993)).

Immunoprecipitation: Rabbit antiserum for ABCA-1 is raised against a synthetic peptide corresponding to the deduced peptide KNQTVVDAVLTSFLQDEKVKES located at the C-terminus of human ABCA-1. Immunoprecipitation is performed by solubilizing the cells in PBS containing 1% Triton X-100 (Sigma, St. Louis, Mo.) and protease inhibitors leupeptin (1 mM), pepstatin (1 mM), and aprotinin (1 mM). The cell extract is incubated overnight at 4° C. with anti-ABCA-1 antiserum at 1:200 dilution followed by an additional 1 hour incubation with 5 µl proteinA-coated magnetic beads (Dynal, Lake Success, N.Y.; Cat. #1001.01). The antibody-antigen complex is sedimented with a magnet, the beads are ished twice with 1% Triton-X/PBS, and the proteins are eluted with 1% acetic acid.

Detection of ABCA-1 Protein: The eluted biotinylated proteins are subjected to SDS-PAGE (6% gel; 150V, 5 hours) and transferred to nitrocellulose membrane (200 mA, 18 hours). The nitrocellulose is probed with streptavidin-horse radish peroxidase (Amersham Pharmacia, Piscataway, N.J.; Cat. #RPN 1231) diluted 300-fold and detected by enhanced chemiluminescence labeling (ECL) according to vendor's protocol (Amersham Pharmacia, Piscataway, N.J.). To test for possible biotinylation of intracellular proteins, the post-immunoprecipitation supernatant is treated with a mouse monoclonal antibody to the intracellular protein β-COP and immunoprecipitated biotinylated β-COP is assayed by streptavidin blotting.

EXAMPLE 20

The ability of the compounds of the invention to stimulate cholesterol efflux from cells was determined in the following assay.

RAW 264.7 cells were loaded with cholesterol as described in Smith et al., J. Biol. Chem., 271:30647–30655 (1996). Briefly, semi-confluent cells plated in 48-well dishes were incubated in 0.2 ml of DMEM supplemented with 4.5 g/L glucose, 0.1 g/L sodium pyruvate and 0.584 g/L of glutamine, 10% fetal bovine serum, 50 µg/ml acetylated low density lipoprotein (AcLDL) and 0.5 µCi/ml of [$^3$H]-cholesterol. After 18 hr, cells were washed two times with PBS containing 1% BSA and incubated overnight (16–18 hours) in DMEM/1% BSA to allow for equilibration of cholesterol pools. The cells were then rinsed four times with PBS/BSA and incubated for one hour at 37° C. with DMEM/BSA. Efflux medium (DMEM/BSA) containing either albumin alone (control), albumin plus HDL (40 µg protein/ml), or albumin plus apo A-I (20 µg/ml, Biodesign International, Kennebunk, Me.) was added and the cells were incubated for 4, 24, or 48 hours.

Cholesterol efflux was measured by removing the medium, washing the cell layer and extracting the cells. Cellular radioactivity was measured by scintillation counting after solubilization in 0.5 ml of 0.2M NaOH (Smith et al., J. Biol. Chem., 271:30647–30655 (1996)) or extraction in hexane:isopropanol (3:2 v/v) as described in Francis et al., J. Clin. Invest., 96, 78–87 (1995). The labelled phospholipid remaining in the medium was also determined by liquid scintillation counting. The efflux of cholesterol was expressed as the percentage of tritiated lipid counts in the medium over the total tritiated lipid counts recovered from the cells and medium (cpm medium/cpm (medium+lysate)× 100).

Cholesterol efflux was also determined in THP cells. Replicate cultures of THP cells were plated in 48 well dishes using the method described (see Kritharides et al Thrombo Vasc Biol 18, 1589–1599, 1998). Cells were plated at an initial density of 500,000 cells/well. After addition of PMA (100 ng/ml), the cultures were incubated for 48 hr at 37° C. The medium was aspirated and replaced with RPMI-1640 medium containing 2 mg/ml of FAFA, 50 μg/ml of acetylated LDL and 3 μCi/ml of radiolabeled cholesterol. After an overnight incubation, the medium was aspirated, the wells washed extensively with PBS. 0.2 ml of RPMI-1640 medium containing 2 mg/ml of FAFA was added to each well. The compound of interest was added to a final concentration of 10 μM. After 4 hr, Apolipoprotein Al (10 μg/ml) was added to some wells and the cultures incubated for 24 hr. The medium was harvested and assayed for radioactivity. The amount of radioactivity in the cell layer was ascertained by adding 0.2 ml of 2 M NaOH and counting the lysed cells. The percent cholesterol efflux was calculated as described above.

The compounds of the invention stimulated cholesterol efflux in this assay.

EXAMPLE 21

The relationship between ABCA-1 expression and HDL levels are determined in the following in vivo assay.

Candidate compounds that increase ABCA-1 expression in vitro and are pharmacologically active and available in vivo are administered daily at a predetermined dosage to 7 week old male C57B1/6 mice either by intraperitoneal injection or by gavage in 10% Cremaphore (BASF)/saline. Three to 4 hours after the final injection, fasted EDTA-plasma and appropriate tissues are collected for analysis. Plasma HDL is isolated by phosphotungstic acid precipitation (Sigma) and HDL cholesterol, total cholesterol and triacylglycerols are determined enzymatically using kits (Roche Diagnostics). Changes to HDL cholesterol and size are further analyzed by FPLC using two Superose 6/30 columns connected in series with cholesterol in the eluted fractions detected enzymatically. In vivo changes in ABCA-1 gene expression are further confirmed by RT-PCR analysis of RNA isolated from candidate tissues.

A correlation between ABCA-1 expression and HDL levels was observed in this assay.

What is claimed is:

1. A compound of the Formula I

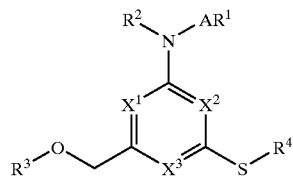

Formula I wherein:
A is a covalent bond;
$R^1$ and $R^2$ are hydrogen;
$R^3$ is optionally substituted alkyl, optionally substituted cycloalkyl, optionally substituted heterocyclyl, optionally substituted aryl, or optionally substituted heteroaryl; and
$R^4$ is hydrogen, optionally substituted alkyl, optionally substituted cycloalkyl, optionally substituted heterocyclyl, optionally substituted aryl, or optionally substituted heteroaryl;
with the proviso that
when $R^4$ is methyl or ethyl, $R^3$ cannot be lower alkyl or unsubstituted phenyl.

2. The compound of claim 1, wherein $R^3$ is optionally substituted aryl or optionally substituted heteroaryl.

3. The compound of claim 2, wherein $R^3$ is optionally substituted phenyl.

4. The compound of claim 3, wherein $R^4$ is alkyl of 1–8 carbon.

5. The compound of claim 4, wherein $R^3$ is 4-t-butylphenyl and $R^4$ is methyl, namely 6-{[4-(tert-butyl)phenoxy]methyl}-4-pentylthio-1,3,5-triazine-2-ylamine.

6. The compound of claim 4, wherein $R^3$ is 4-t-butylphenyl and $R^4$ is n-pentyl, namely 6-{[4-(tert-butyl)phenoxy]methyl}-4-pentylthio-1,3,5-triazine-2-ylamine.

7. The compound of claim 4, wherein $R^3$ is 3-chlorophenyl, $R^4$ is methyl, and $R^5$ is hydrogen, namely 4-[(3-chlorophenylamino)methyl]-6-methylthio-[1,3,5]triazin-2-ylamine.

8. The compound of claim 4, wherein $R^3$ is 2,4-dimethoxyphenyl, $R^4$ is methyl, and $R^5$ is hydrogen, namely N-{[(3,5-dimethoxyphenyl]aminomethyl}-4-methylthio-1,3,5-triazine-2-ylamine.

9. A pharmaceutical composition comprising at least one pharmaceutically acceptable excipient and a therapeutically effective amount of a compound of claim 1.

10. A method of treating atherosclerosis in a mammal comprising administering to a mammal in need thereof a therapeutically effective dose of a compound of Formula I:

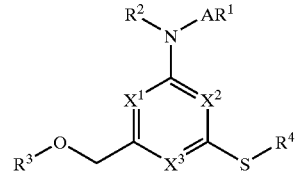

Formula I wherein:
A is a covalent bond;
$R^1$ and $R^2$ are hydrogen;
$R^3$ is optionally substituted alkyl, optionally substituted cycloalkyl, optionally substituted heterocyclyl, optionally substituted aryl, or optionally substituted heteroaryl; and
$R^4$ is hydrogen, optionally substituted alkyl, optionally substituted cycloalkyl, optionally substituted heterocyclyl, optionally substituted aryl, or optionally substituted heteroaryl.

11. The method of claim 10, wherein $R^4$ is optionally substituted alkyl.

12. The method of claim 11, wherein $R^3$ is optionally substituted aryl or optionally substituted heteroaryl.

13. The method of claim 12, wherein $R^3$ is optionally substituted phenyl.

14. The method of claim 13, wherein $R^4$ is alkyl of 1–8 carbon atoms.

15. The method of claim 14, wherein $R^3$ is 4-t-butylphenyl and $R^4$ is methyl, namely 6-{[4-(tert-butyl)phenoxy]methyl}-4-methylthio-1,3,5-triazine-2-ylamine.

16. The method of claim 14, wherein $R^3$ is 4-t-butylphenyl and $R^4$ is n-pentyl, namely 6-{[4-(tert-butyl)phenoxy]methyl}-4-pentylthio-1,3,5-triazine-2-ylamine.

17. The method of claim 14, wherein $R^3$ is 3-chlorophenyl, $R^4$ is methyl, and $R^5$ is hydrogen, namely 4-[(3-chlorophenylamino)methyl]-6-methylthio-[1,3,5]triazin-2-ylamine.

18. The method of claim 14, wherein $R^3$ is 2,4-dimethoxyphenyl, $R^4$ is methyl, and $R^5$ is hydrogen, namely N-{[(3,5-dimethoxyphenyl]aminomethyl}-4-methylthio-[1,3,5]-triazine-2-ylamine.

19. The method of claim 10, further comprising coadministration of a therapeutically effective amount of a compound that lowers LDL cholesterol.

20. The method of claim 19, wherein the LDL cholesterol lowering compound is chosen from clofibrate, gemfibrozil, and fenofibrate, nicotinic acid, mevinolin, mevastatin, pravastatin, simvastatin, fluvastatin, lovastatin, cholestyrine, colestipol and probucol.

* * * * *